(12) United States Patent
Suzuki et al.

(10) Patent No.: US 10,959,706 B2
(45) Date of Patent: Mar. 30, 2021

(54) PHANTOM FOR ULTRASOUND MEASUREMENT, AND ULTRASOUND CT DEVICE

(71) Applicant: HITACHI, LTD., Tokyo (JP)

(72) Inventors: Atsuro Suzuki, Tokyo (JP); Kenichi Kawabata, Tokyo (JP); Takahide Terada, Tokyo (JP); Yushi Tsubota, Tokyo (JP); Wenjing Wu, Tokyo (JP); Kazuhiro Yamanaka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 487 days.

(21) Appl. No.: 15/894,115

(22) Filed: Feb. 12, 2018

(65) Prior Publication Data
US 2018/0310923 A1 Nov. 1, 2018

(30) Foreign Application Priority Data
Apr. 26, 2017 (JP) .............................. JP2017-087181

(51) Int. Cl.
*A61B 8/00* (2006.01)
*A61B 6/03* (2006.01)
(Continued)

(52) U.S. Cl.
CPC .............. *A61B 8/587* (2013.01); *A61B 6/032* (2013.01); *A61B 8/085* (2013.01); *A61B 8/0825* (2013.01);
(Continued)

(58) Field of Classification Search
CPC ........... A61B 8/587; A61B 8/15; A61B 8/085; A61B 6/032; A61B 8/0825; A61B 8/546; A61B 8/4416; G09B 23/286; G09B 23/30
(Continued)

(56) References Cited

U.S. PATENT DOCUMENTS

| | | | | |
|---|---|---|---|---|
| 4,331,021 A | * | 5/1982 | Lopez | A61B 8/587 73/1.86 |
| 4,985,906 A | * | 1/1991 | Arnold | A61B 6/583 378/18 |

(Continued)

FOREIGN PATENT DOCUMENTS

WO WO-2015194575 A1 * 12/2015 ........... A61B 5/7203

OTHER PUBLICATIONS

J. Nebeker, T. R. Nelson, "Imaging of Sound Speed Using Reflection Ultrasound Tomography", J Ultrasound Med 2012; 31:1389-1404 (Year: 2012).*

(Continued)

*Primary Examiner* — Jeffrey G Hoekstra
*Assistant Examiner* — Renee C Langhals
(74) *Attorney, Agent, or Firm* — Procopio, Cory, Hargreaves & Savitch LLP

(57) ABSTRACT

Provided herein is a phantom capable of mimicking both a dense breast and a fatty breast. A phantom for ultrasound measurement includes: a first member that mimics an object of interest for measurement; and a second member having provided therein the first member. The second member has the property to decrease its sound speed with a temperature increase brought by external temperature control. The sound speed of the second member at a predetermined temperature is equal to the sound speed of a third member surrounding the second member. The first member and the second member are immiscible with each other.

13 Claims, 14 Drawing Sheets

(51) Int. Cl.
*A61B 8/08* (2006.01)
*G09B 23/30* (2006.01)
*G09B 23/28* (2006.01)
*A61B 8/15* (2006.01)

(52) U.S. Cl.
CPC .............. *A61B 8/15* (2013.01); *G09B 23/286* (2013.01); *G09B 23/30* (2013.01); *A61B 8/4416* (2013.01); *A61B 8/546* (2013.01)

(58) Field of Classification Search
USPC ........................................................ 600/437
See application file for complete search history.

(56) References Cited

U.S. PATENT DOCUMENTS

| | | | |
|---|---|---|---|
| 2004/0077943 A1* | 4/2004 | Meaney | A61B 5/05 600/430 |
| 2016/0180745 A1* | 6/2016 | Trotta | B29C 39/10 434/267 |

OTHER PUBLICATIONS

Madsen, E.L., Dong, F., Frank, G.R., Garra, B.S., Wear, K.A., Wilson, T., Zagzebski, J.A., Miller, H.L., Shung, K.K., Wang, S.H. and Feleppa, E.J., "Interlaboratory comparison of ultrasonic backscatter, attenuation, and speed measurements", 1999, Journal of ultrasound in medicine, 18(9), pp. 615-631. (Year: 1999).*

Niebeker, J. and Nelson, T., "Imaging of Sound Speed Using Reflection Ultrasound Tomography", J Ultrasound Med, 2012, pp. 1389-1404, vol. 31. (2012).

Glide, C., et al., "Novel Approach to Evaluating Breast Density Utilizing Ultrasound Tomography", Medical Physics, Jan. 30, 2007, pp. 744-753, vol. 34 (2).

Oudry, J., et al., "Copolymer-in-oil Phantom Materials for Elastography", Ultrasound in Medicine and Biology, Jan. 26, 2009, pp. 1185-1197, vol. 35(7).

Browne, J. et al., "Assessment of the Acoustic Properties of Common Tissue-mimicking Test Phantoms", Ultrasound in Medicine and Biology, Jan. 1, 2003, pp. 1053-1060, vol. 29(7), Dublin, Ireland.

Maggi, L. et al., "Ultrasonic Attenuation and Speed in Phantoms Made of PVCP and Evaluation of Acoustic and Thermal Properties of Ultrasonic Phantoms Made of polyvinyl chloride-plastisol (PVCP)", IWBBIO 2013 Proceedings, Mar. 18-20, 2013, pp. 233-241, Granada.

* cited by examiner (a)

(b)

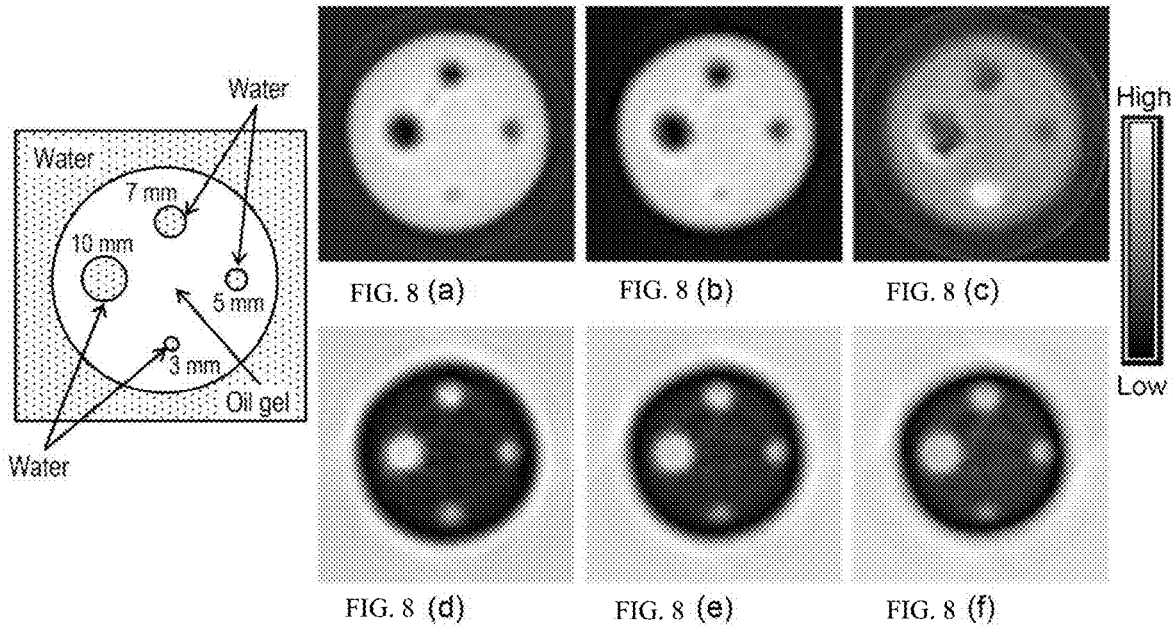
FIG. 8 (a) FIG. 8 (b) FIG. 8 (c)
FIG. 8 (d) FIG. 8 (e) FIG. 8 (f)
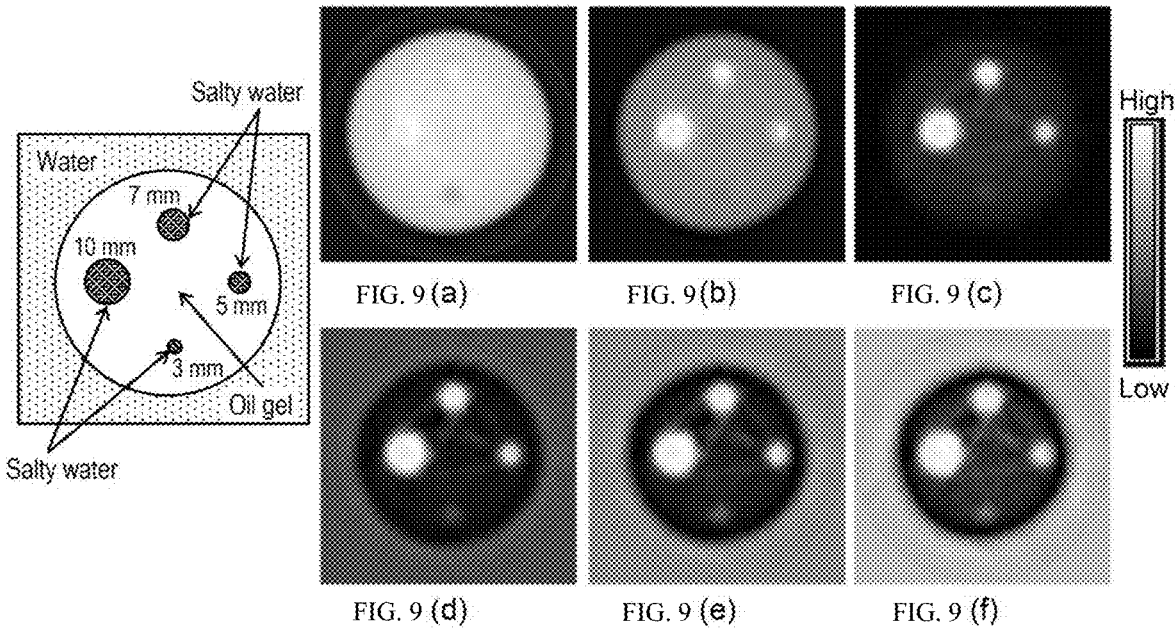
FIG. 9 (a) FIG. 9 (b) FIG. 9 (c)
FIG. 9 (d) FIG. 9 (e) FIG. 9 (f)

PHANTOM FOR ULTRASOUND MEASUREMENT, AND ULTRASOUND CT DEVICE

CLAIM OF PRIORITY

The present application claims priority from Japanese patent application JP 2017-087181 filed on Apr. 26, 2017, the content of which is hereby incorporated by reference into this application.

TECHNICAL FIELD

The present invention relates to a phantom for ultrasound measurement, and an ultrasound CT device.

BACKGROUND ART

A breast dedicated ultrasound CT (computed tomography) device is available as a medical diagnostic device used for the ultrasound detection of breast cancer. The ultrasound CT device uses an ultrasound transmitter and receiver that are disposed around a breast placed in water. With the ultrasound transmitter and receiver, the device measures the all-round ultrasound reflected signal and transmitted signal, and a tomographic image of breast is obtained upon image reconstruction. The reflected signal provides information concerning the structures of breast tissue. The transmitted signal provides information concerning the sound speed and the attenuation of ultrasound in the tissue.

As a rule, ultrasound has a higher sound speed and attenuation in tumor than in normal tissue such as the mammary gland and the fat surrounding a tumor. A tomographic image of ultrasound speed or attenuation thus enables quantitative detection of tumor.

CITATION LIST

Non Patent Literature

NPL 1: J Ultrasound Med 2012, 31; 1389-1404
NPL 2: Medical Physics 2007, 34; 744-753
NPL 3: Ultrasound in Med. & Biol., 2009, 35; 1185-1197
NPL 4: Ultrasound in Med. & Biol., 2003, 29; 1053-1060
NPL 5: IWBBIO 2013. Proceedings, 233-241

SUMMARY OF INVENTION

Technical Problem

The high accuracy of quantitative measurement of ultrasound speed or attenuation in tissue using an ultrasound CT device is very important in determining whether a tumor is benign or malignant. Accuracy control is therefore essential for making the ultrasound CT device reliable as a diagnostic device, and this requires a regularly performed quantitative evaluation using a phantom that mimics the acoustic properties of the body.

For accuracy control, a phantom is required to mimic the acoustic properties of the body, and to maintain the same quantitative value over extended time periods. A polyacrylamide gel is available as a phantom for evaluating the performance of an ultrasound CT device. Nebeker et al. uses a phantom made out of a cylindrical polyacrylamide gel having formed therein rod-like voids as a region of interest. The voids in the phantom contain fluids such as water, oil, and ethanol (NPL 1). The polyacrylamide gel mimics the background region, or the normal breast tissue, and the fluid mimics the region of interest, or the tumor. A notable characteristic of the phantom introduced in NPL 1 is the use of fluids having different sound speeds, enabling the tumor-mimicking region of interest to have different sound speeds.

The breast is composed of primarily the mammary gland and fat. Dense breasts, which have more gland tissue and less fat tissue, have a sound speed of 1,560 [m/s], whereas more fatty and less glandular fatty breasts have a sound speed of 1,380 [m/s] (NPL 2). For imaging of a breast in 35-degree Celsius water, the sound speed of water is 1,520 [m/s]. That is, the background region of a dense breast has a higher sound speed than water. The background region of a fatty breast, on the other hand, has a lower sound speed than water.

Imaging of a phantom with an ultrasound CT device takes place with the phantom being placed in water, as in imaging of the actual breast. In the phantom of Nebeker et al. using a polyacrylamide gel, the polyacrylamide gel has a higher sound speed than water, and the background region mimics a dense breast, which has a higher sound speed than background water. While the phantom using a polyacrylamide gel is able to mimic a dense breast, mimicking of a fatty breast is not possible with a polyacrylamide gel. A polyacrylamide gel also easily deteriorates, and is not suited for a regular quantitative evaluation using the same phantom.

The present invention is intended to provide a solution to the foregoing problems, and it is an object of the present invention to provide a phantom that can mimic both a dense breast and a fatty breast.

Solution to Problem

As an example, the configuration recited in the claims is used to solve the foregoing problems. The present patent application contains more than one means to solve the foregoing problems, and one example of such means is a phantom for ultrasound measurement that includes: a first member that mimics an object of interest for measurement; and a second member having provided therein the first member, the second member having the property to decrease its sound speed with a temperature increase brought by external temperature control, the sound speed of the second member at a predetermined temperature being equal to a sound speed of a third member surrounding the second member, the first member and the second member being immiscible with each other.

Advantageous Effects of Invention

The present invention can provide a phantom that is capable of mimicking a dense breast with the background region that has a higher sound speed than water at a temperature below a predetermined temperature $T_0$, and that is capable of mimicking a fatty breast with the background region that has a lower sound speed than water at a temperature higher than $T_0$. Other features concerning the present invention will be more clearly understood from the following descriptions and the accompanying drawings. Other problems, configurations, and effects will be apparent from the descriptions of the embodiments below.

BRIEF DESCRIPTION OF DRAWINGS

FIGS. 8(a)-8(f) show sound speed reconstruction images of a phantom with water filling the inclusion region.

FIGS. 9(a)-9(f) show diagrams representing sound-speed reconstruction images of a phantom with salty water (3.5%) filling the inclusion region.

DESCRIPTION OF EMBODIMENTS

Embodiments of the present invention are described below with reference to the accompanying drawings. The drawings represent specific embodiments based on the principle of the present invention. However, the embodiments are intended to help understand the present invention, and are not to be construed to limit the present invention.

The following embodiments are related to a phantom used for performance evaluation or correction of an ultrasound CT device. A typical configuration of an ultrasound CT device is described first, followed by how the relative refractive index of an object against the background water affects collection in imaging by an ultrasound CT device. A phantom for ultrasound measurement capable of mimicking both a dense breast and a fatty breast will be described last.

Figure 1:
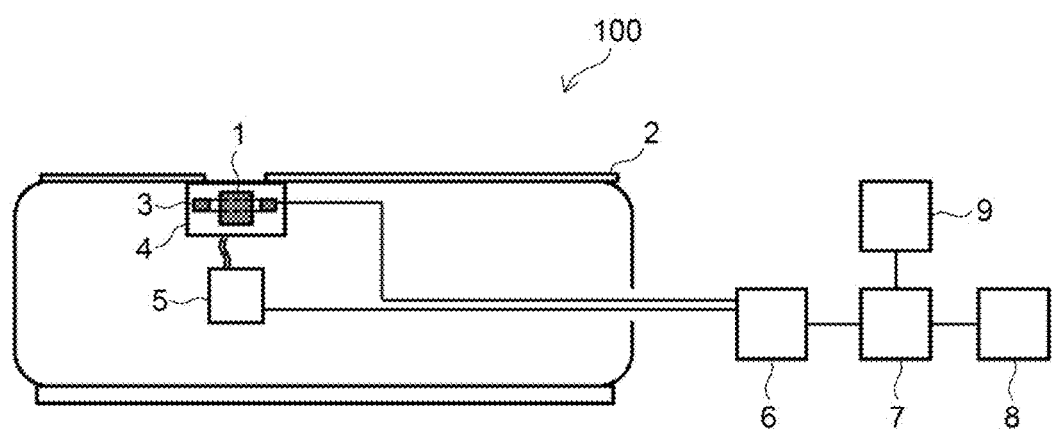
FIG. 1 is a diagram representing the configuration of an ultrasound CT device according to an embodiment.

FIG. 1 is a diagram representing the configuration of an ultrasound CT device according to an embodiment. An ultrasound CT device 100 includes a bed 2 on which a subject lies face-down, an ultrasound transmitter and receiver unit array module 3 provided with an array of ultrasound transmitter and receiver units, a water tank 4 to which an object such as a breast and a phantom 1 is inserted, an auxiliary tank 5 for supplying water to the water tank 4, a controller 6 for executing the data collected by the ultrasound transmitter and receiver unit array module 3, and adjusting the temperature of the water inside the auxiliary tank 5, a signal processor 7 for imaging the collected data, a memory section 8 for storing the collected data and the image, and an input-output section 9 for inputting commands and outputting an image.

The controller 6, the signal processor 7, and the memory section 8 may be provided by a general-purpose computer. The computer includes a processor such as a CPU (Central Processing Unit), a memory, and an auxiliary memory device such as hard disc. The processes of the controller 6 and the signal processor 7 may be implemented as functions of a program executed on the computer. The input-output section 9 is configured from, for example, an input section such as a keyboard and a pointing device (e.g., a mouse), and a display section such as a display.

Figure 2:
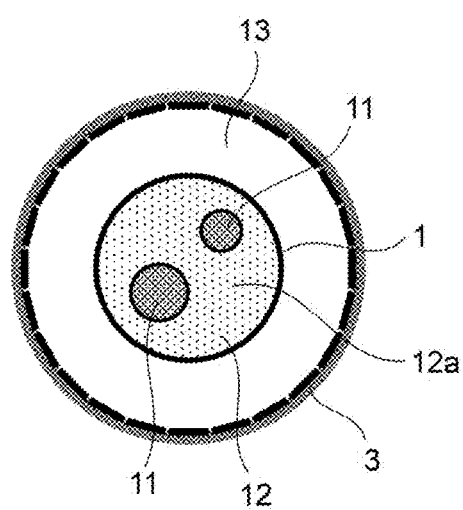
FIGS. 2(a) and 2(b) show diagrams representing an ultrasound transmitter and receiver unit array module, and a phantom according to an embodiment.
Figure 2:
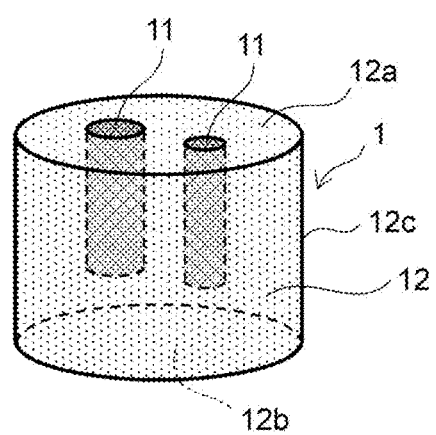

FIG. 2(a) is a diagram representing the ultrasound transmitter and receiver unit array module 3 according to the embodiment. The ultrasound transmitter and receiver unit array module 3 includes a ring-like array of ultrasound transmitter and receiver units. The ultrasound transmitter and receiver units transmit ultrasound of a frequency of about several megahertz. The ultrasound is incident on the object in water. A part of the incident ultrasound is reflected on the object's surface or on surfaces of the structure inside the object, and the reflected waves are received by the ultrasound transmitter and receiver units. Other part of the ultrasound passes through the object by being repeatedly refracted on the object's surface or inside the object, and the transmitted waves are received by the ultrasound transmitter and receiver units. This series of ultrasound transmissions and receptions takes place from all directions around the object. The signal processor 7 performs an image reconstruction process for the received signals of reflected waves, and acquires a tomographic image representing the boundaries of a structure. The signal processor 7 performs an image reconstruction process also for the received signals of transmitted waves, and acquires two tomographic images representing the sound speed and the attenuation, respectively, of the ultrasound in the object. A three-dimensional image of the object is created as the ultrasound transmitter and receiver unit array module 3 collects the reflected waves and the transmitted waves by moving up and down in vertical direction.

FIG. 2(b) is a perspective view of the phantom 1 according to the embodiment. The phantom 1 includes at least one first member 11 that mimics an object of interest for measurement, and a second member 12 having provided therein the first member 11. The second member 12 is columnar in shape, and has a first surface 12a at the top, a second surface 12b at the bottom on the opposite end, and a side surface 12c. The first member 11 is columnar in shape, with one end of the columnar shape being exposed at the first surface 12a. The first member 11 is a liquid, for example, such as water, and salty water. The second member 12 is surrounded by a third member 13 (for example, water), as shown in FIG. 2(a). The first member 11 may be embedded in the second member 12 without being exposed at a surface of the second member 12, as will be described later. The properties of the first member 11 and the second member 12 also will be described later.

The following describes how the relative refractive index of the object against the background water affects collection in imaging by the ultrasound CT device 100. Because the object is in water in the ultrasound CT device 100, the transmitted ultrasound is received by the ultrasound transmitter and receiver units by first passing through water, and then the object, and again through water. Here, the sound speed difference between the object and the background water affects the position at which the transmitted waves are received. This is because the refraction of waves is determined by the sound speed difference between different media.

Figure 3:
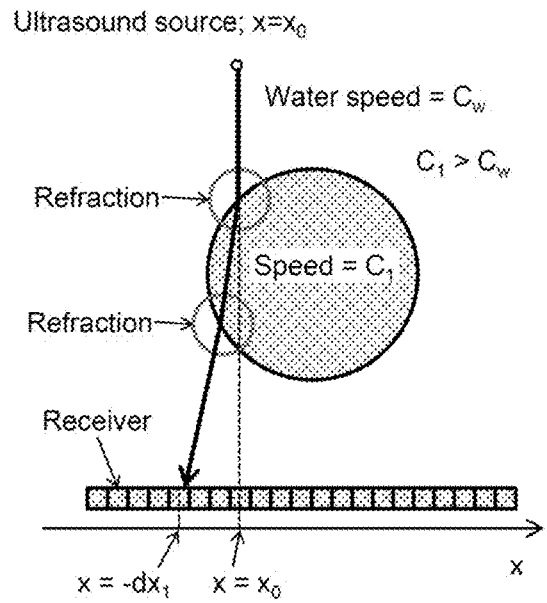
FIGS. 3(a) and 3(b) show diagrams representing the wave trajectory of ultrasound passing through an object in water.
Figure 3:
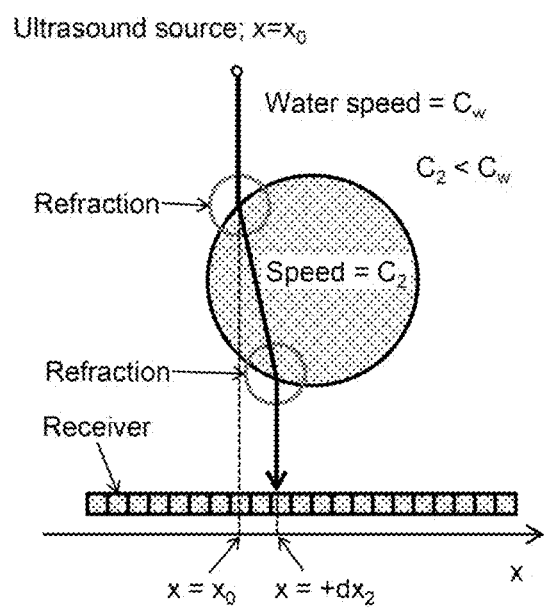

FIG. 3 shows diagrams representing the trajectory of ultrasound passing through the object in water. FIG. 3(a) is a diagram in which the sound speed $C_1$ of the object is higher than the sound speed $C_w$ of the background water. In FIG. 3(b), the sound speed $C_2$ of the object is lower than the sound speed $C_w$ of the background water. FIG. 3(a) shows how the ultrasound propagates from a source ($x=x_0$) toward the receiver unit (receiver), and is refracted twice at the object. Here, the transmitted waves are received at the position $x=-dx_1$. In FIG. 3 and elsewhere, the receiver unit (receiver) means a receiver unit of the ultrasound transmitter and receiver unit array module 3.

In FIG. 3(b), the transmitted waves are received at the position $x=+dx_2$. As shown in these figures, the ultrasound generated and transmitted from the same location falls in different positions as determined by the refraction between the object and the background water. The relative refractive index of the object against water thus affects the positional information of transmitted waves in the collected data, and the final image reconstruction result.

Figure 4:
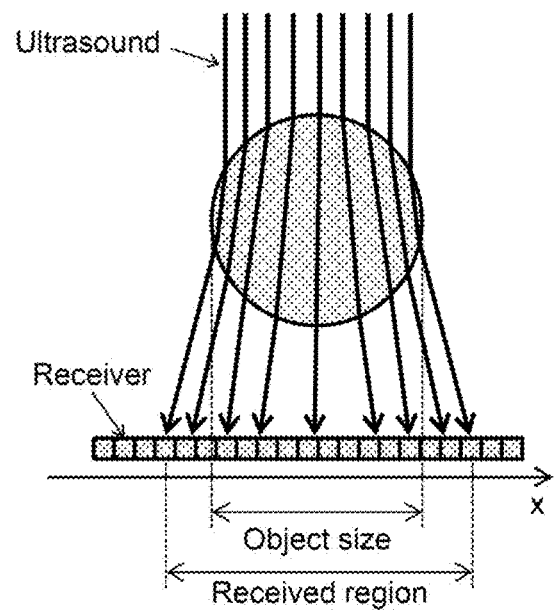
FIGS. 4(a) and 4(b) show diagrams depicting the region of the receiver unit receiving transmitted waves.
Figure 4:
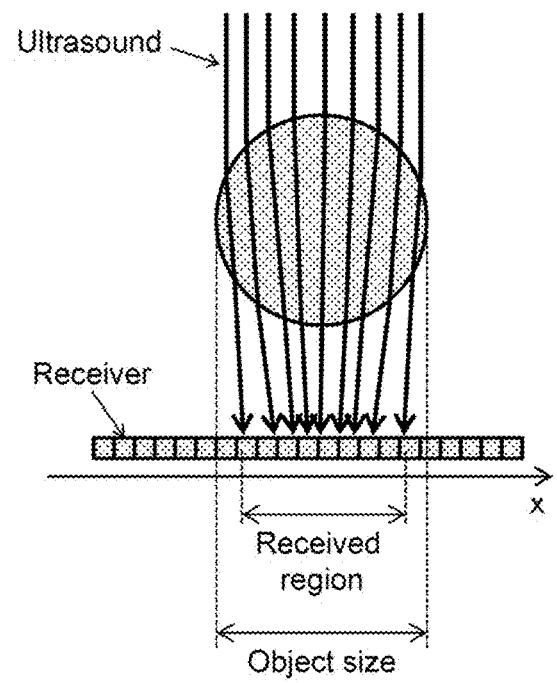

FIG. 4 shows diagrams depicting the region of the receiver unit receiving the transmitted waves. As shown in FIG. 4(a), the transmitted waves are received over a region of the receiver unit wider than the size of the object when the sound speed of the object is higher than the sound speed of the background. When the sound speed of the object is lower than the sound speed of the background, the transmitted waves are received in a region of the receiver unit narrower than the object size, as shown in FIG. 4(b). When the collected data from FIGS. 4(a) and 4(b) are reconstructed by FBP (Filtered Back Projection), which is a reconstruction technique that does not take into account refraction of waves, the object's size created by the signal processor 7 for the data collected in FIG. 4(a) and FIG. 4(b) appears larger and smaller, respectively, than the actual size.

The following describes a phantom for ultrasound measurement capable of mimicking both a dense breast and a fatty breast. The property of the phantom 1 according to the embodiment is such that the first member 11 that mimics an object of interest for measurement is immiscible with the second member 12, and vice versa. The second member 12 has the property to decrease its sound speed with a temperature increase brought by external temperature control, and the sound speed of the second member 12 at a predetermined temperature is equal to the sound speed of the third member 13 (for example, water in the water tank 4) surrounding the second member 12.

In the present embodiment, an oil gel is used as the material of the second member 12 of the phantom 1. The oil gel is produced by mixing a paraffin oil with a polymer called SEBS (Styrene-Ethylene/Butylenes-Styrene). In the present embodiment, the oil gel was produced by dissolving SEBS in a paraffin oil being stirred on a 175° C. hot plate, and cooling the mixture at ordinary temperature after deaeration.

Figure 5:
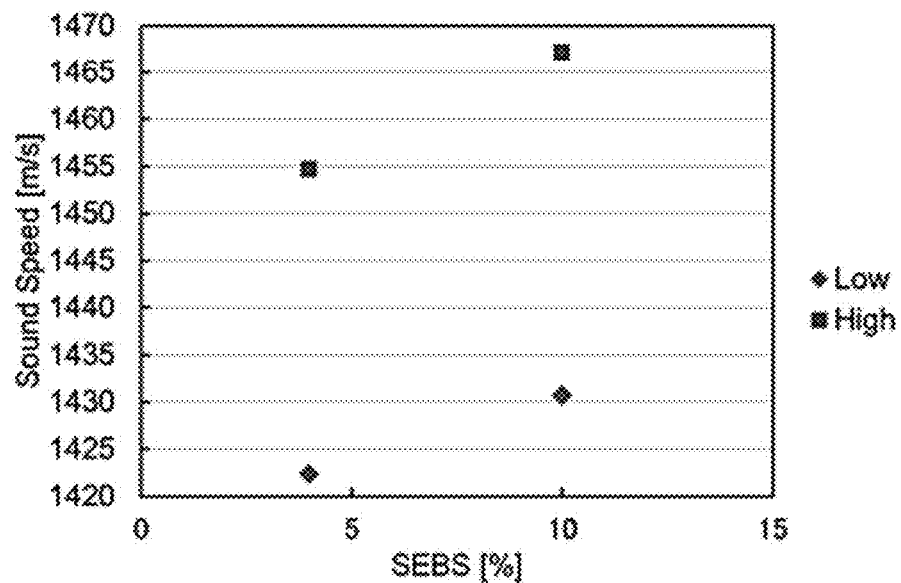
FIGS. 5(a) and 5(b) show diagrams representing the sound speed and the attenuation rate of an oil gel.
Figure 5:
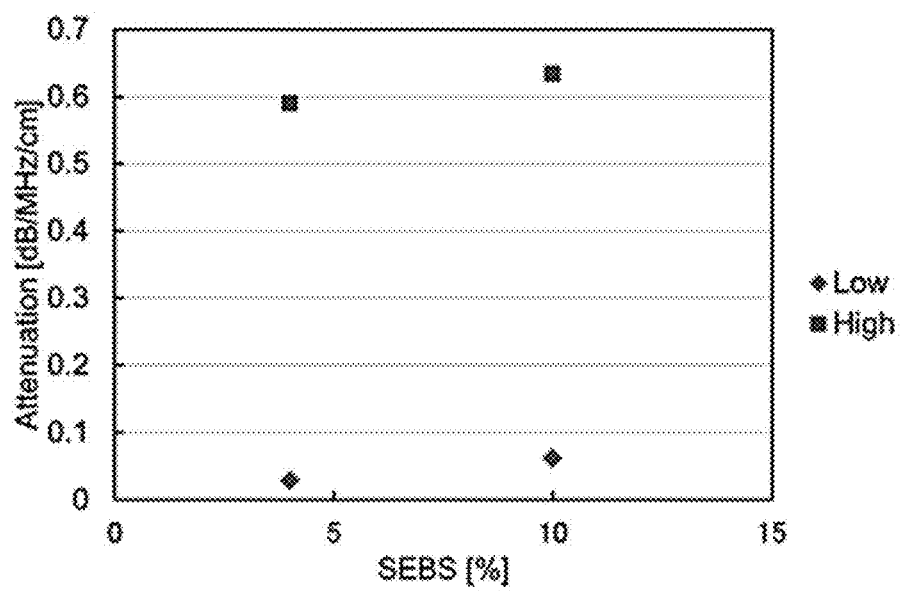

FIG. 5 shows diagrams representing basic properties of the oil gel, specifically, the sound speed and the attenuation rate of the oil gel. FIG. 5(a) shows the sound speed of oil gel for 4% and 10% weight concentrations of SEBS. FIG. 5(b) shows the attenuation rate of oil gel for 4% and 10% weight concentrations of SEBS. The oil gel had a temperature of 25° C., and the legends "High" and "Low" in the figures mean that the paraffin oil has a high kinetic viscosity and a low kinetic viscosity, respectively. As can be seen, the sound speed and the attenuation rate increase with increasing weight concentrations of SEBS. The oil gel can be produced with a 2% to 16% weight concentration range of SEBS; however, the viscosity increases, and the oil gel cannot be easily dissolved in the paraffin oil when the weight concentration becomes higher than 16% (NPL 3). In the present embodiment, the phantom 1 was produced using an oil gel that was prepared by adding SEBS (weight concentration: 10%) to a paraffin oil of a high kinetic viscosity.

Figure 6:
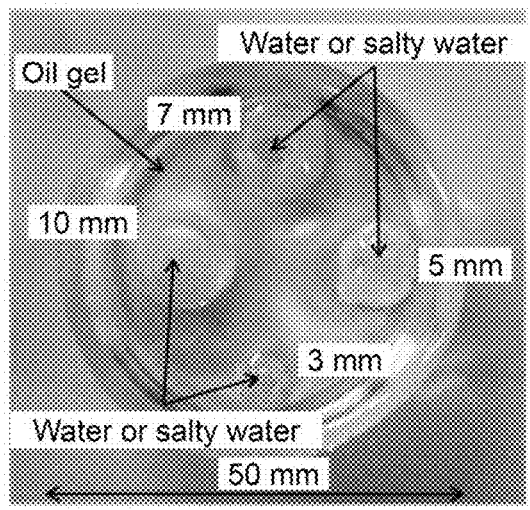
FIG. 6 shows a diagram of a phantom using an oil gel according to an embodiment.

FIG. 6 shows a photograph of the phantom using the oil gel. The phantom 1 has a columnar shape with a diameter of 50 mm. Inside the oil gel (second member 12), the phantom 1 has cylindrical holes measuring 10, 7, 5, and 3 mm. The cylindrical holes can accommodate a solution, and the solution represents the first member 11 of the phantom 1. The region filled with the solution is a region, or an inclusion region as it is also called, mimicking an object of interest for measurement, which may be a tumor or a tumor mass.

A feature of the phantom is that the sound speed and the attenuation rate of the inclusion region can be varied by using different solutions. Unlike the polyacrylamide gel, the oil gel has the desirable characteristic that it is not miscible with the solution in the inclusion region. The oil gel region is called a background region, a region mimicking normal tissue such as the mammary gland and the fat of a breast.

Figure 7:
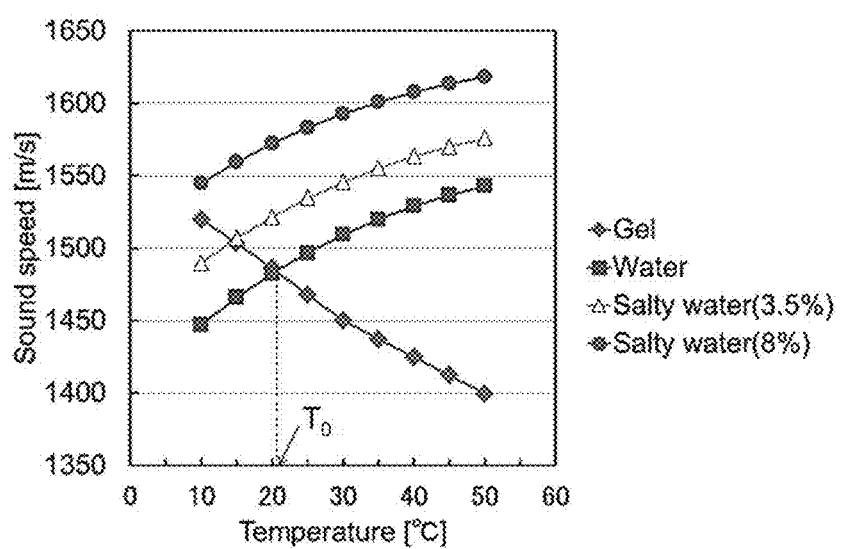
FIG. 7 shows changes in the sound speed of water, salty water, and oil gel against temperature.

FIG. 7 shows changes in the sound speed of water, salty water, and the background oil gel region against temperature. The salty water has two concentrations: 3.5% and 8%. The salty water has a faster sound speed than water. For salty water and water, the sound speed increases with temperature increase. The oil gel, on the other hand, lowers its sound speed with increasing temperatures. That is, the oil gel has the property to decrease its sound speed with a temperature increase brought by external temperature control. It can be seen that the oil gel takes the same sound speed value as water at temperature $T_0$. That is, the oil gel has a higher sound speed than water at a temperature below $T_0$, and a lower sound speed than water at a temperature higher than $T_0$.

Water has a sound speed of 1,520 [m/s] when it has a set temperature of 35 degrees Celsius in clinical imaging of a breast. A dense breast, which has more mammary gland and less fat, has a sound speed of 1,560 [m/s], and a fatty breast, which has more fat and less mammary gland, has a sound speed of 1,380 [m/s] (NPL 2). In imaging of a dense breast using the ultrasound CT device, the breast has a higher sound speed than the background water. In the case of a fatty breast, the breast has a lower sound speed than the background water. That is, by imaging the oil gel phantom 1 at a temperature below $T_0$, the relative refractive index of the background oil gel region against the background water can be set to the value of when imaging a dense breast. Conversely, with the phantom 1 imaged at a temperature higher than $T_0$, the relative refractive index of the background oil gel region against the background water can be set to the value of when imaging a fatty breast.

The phantom 1 is disposed in the water tank 4, and the water surrounds the phantom 1. At the predetermined temperature $T_0$, the oil gel (second member 12) has the same sound speed as the water (third member 13) surrounding the oil gel. As described above, the phantom 1 can mimic both a dense breast and a fatty breast by increasing and decreasing the temperature above and below $T_0$. The third member 13 surrounding the oil gel is water in the present embodiment. However, the invention is not limited to this. A material that takes the same sound speed as the oil gel at the predetermined temperature also may be used instead of water.

FIG. 8 shows sound speed reconstruction images of the phantom with water filling the inclusion region. In FIG. 8, the images (a), (b), (c), (d), (e), and (f) are images for temperatures of 15, 17.5, 20, 22.5, 25, and 27.5 degrees Celsius, respectively. The ultrasound transmitter and receiver unit array module 3 of the ultrasound CT device 100 used to create these images had an inner diameter of 10 cm, and an ultrasound frequency of 1.7 MHz. FBP was used for image reconstruction. It can be seen that the background region has a higher sound speed than the background water for temperatures between 15 and 20 degrees Celsius. For temperatures between 15 and 17.5 degrees Celsius, the inclusion region (water) has a lower sound speed than the background region. For temperatures between 22.5 and 27.5 degrees Celsius, the background region has a lower sound speed than the background water and the inclusion region (water). By comparing the images taken at temperatures of 15 degrees Celsius and 27.5 degrees Celsius, the phantom 1 appears larger for 15 degrees Celsius than for 27.5 degrees Celsius. This is because the transmitted waves are received over a wider region for 15 degrees Celsius, at which the background region has a higher sound speed than the background water, whereas, at 27.5 degrees Celsius, the background region has a lower sound speed than the background water, and the transmitted waves are received over a narrower region. The reconstruction image thus appears larger for 15 degrees Celsius, and smaller for 27.5 degrees Celsius.

FIG. 9 shows diagrams representing sound-speed reconstruction images of the phantom with salty water (3.5%) filling the inclusion region. In FIG. 9, the images (a), (b), (c), (d), (e), and (f) are images for temperatures of 15, 17.5, 20, 22.5, 25, and 27.5 degrees Celsius, respectively. As with the case where the inclusion region is water, the background region has a higher sound speed than the background water for temperatures between 15 and 20 degrees Celsius, and a lower sound speed than the background water for temperatures between 22.5 and 27.5 degrees Celsius. The inclusion region (salty water) has a higher sound speed than the background region for all temperatures between 15 and 27.5 degrees Celsius. It can also be seen that the inclusion region appears larger with increasing temperatures. This is because of the increasing sound speed differences between the inclusion region and the background region, widening the region that receives the ultrasound through the inclusion.

The following descriptions are given from the standpoint of refraction of waves, specifically, how the phantom imaged at different temperatures mimics the refraction of waves for breasts having different sound speeds. Here, the sound speed of water, and the sound speeds of the background region and the inclusion region of the phantom 1 being imaged are represented by $S_w(t)$, $S_{BG}(t)$, and $S_{inc}(t)$, respectively, where t is the temperature. By assuming that the temperature of water for clinical imaging is 35° C., the sound speed of water is $S_w(35)=1,520$ [m/s], and the sound speeds of a breast and a tumor are $S_{br}$ and $S_c$, respectively. In the phantom being imaged, the relative refractive index of the background region for ultrasound against water is $n_1$ ($=S_{BG}(t)/S_w(t)$), and the relative refractive index of the inclusion region for ultrasound against the background region is $n_2$ ($=S_{inc}(t)/S_{BG}(t)$). The relative refractive index of a breast against water in clinical imaging is $n_3$ ($=S_{br}/S_w(35)$), and the relative refractive index of a tumor against the breast is $n_4$ ($=S_c/S_{br}$). The following relation is established by assuming that $n_1$ and $n_3$ are the same.

[Math. 1]

$$\frac{S_{BG}(t)}{S_w} = \frac{S_{br}}{S_w(35)} \tag{1}$$

It follows from this that $S_{br}$ can be determined as follows.

[Math. 2]

$$S_{br} = \frac{S_{BG}(t)}{S_w(t)} \cdot S_w(35) \tag{2}$$

Similarly, the following relation is established by assuming that $n_2$ and $n_4$ are the same.

[Math. 3]

$$\frac{S_{inc}(t)}{S_{BG}(t)} = \frac{S_c}{S_{br}} \tag{3}$$

It follows from this that $S_c$ can be determined as follows.

[Math. 4]

$$S_c = \frac{S_{inc}(t)}{S_{BG}(t)} \cdot S_{br} = \frac{S_{inc}(t)}{S_w(t)} \cdot S_w(35) \tag{4}$$

Figure 10A:
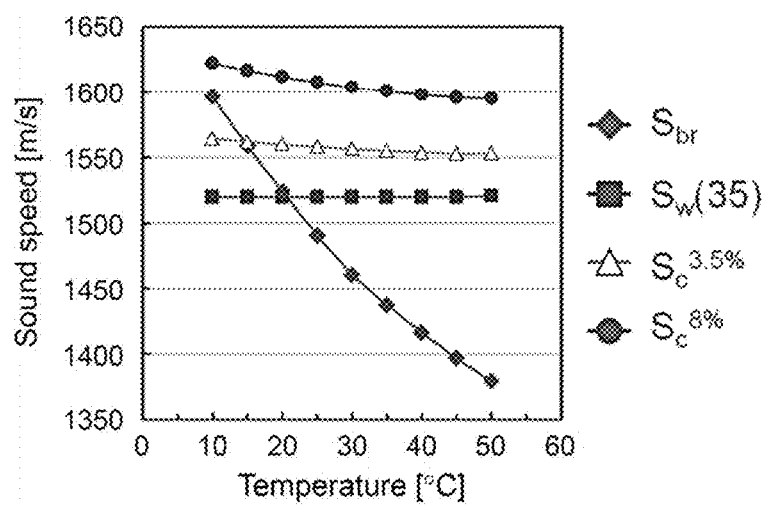
FIGS. 10(a) and 10(b) show diagrams representing the sound speed $S_{br}$ of a breast, and the sound speed $S_c$ of a tumor mimicked by a phantom using an oil gel.
Figure 10B:
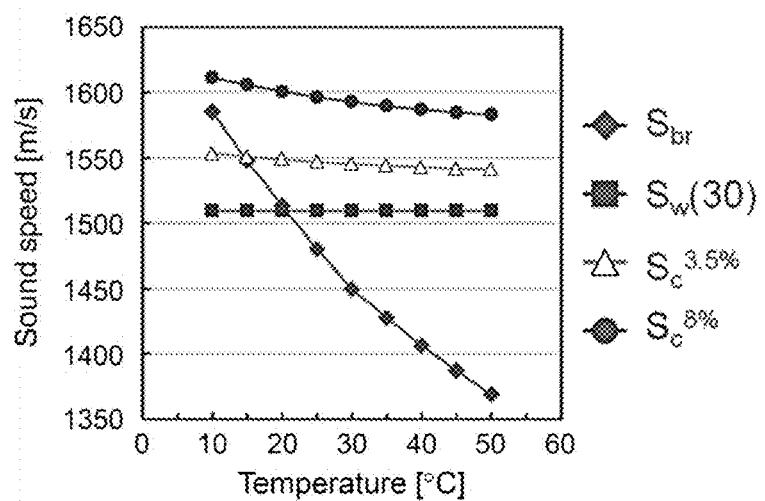

FIG. 10 shows diagrams representing the sound speed $S_{br}$ of a breast, and the sound speed $S_c$ of a tumor mimicked by the phantom using the oil gel. FIGS. 10(a) and 10(b) also show the sound speed of water at 35° C. and 30° C., respectively, in clinical imaging. In the figures, $S_c^{3.5\%}$ and $S_c^{8\%}$ represent the sound speed of a tumor mimicked by the salty water in the inclusion region at salty water concentrations of 3.5% and 8%, respectively. By varying the temperature in a range of 10 to 50° C., it is possible to mimic the refraction against water for a breast having a sound speed of 1,369 to 1,596 [m/s]. Similarly, by varying the temperature in a range of 10 to 50° C., it is possible to mimic the refraction against a breast for a tumor having a sound speed of 1,541 to 1,622 [m/s]. That is, tumors having various sound speeds can be mimicked by making the salty water concentration larger than 0 and 8% or less (0<salty water concentration 8%).

Figure 11:
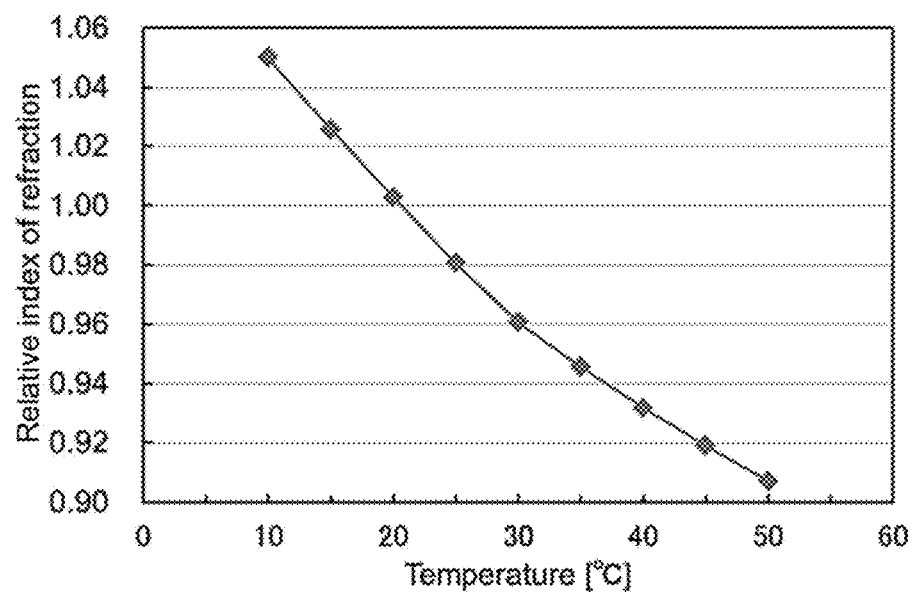
FIG. 11 represents the relative refractive index of an oil gel against water.

FIG. 11 represents the relative refractive index of the oil gel against water. Breasts having various sound speeds can be mimicked by setting a value of 0.9 to 1.05 for the relative refractive index of the oil gel against water. To achieve this, the controller 6 controls the temperature of the water in the water tank 4, and sets a relative refractive index of 0.9 to 1.05 for the oil gel against water. As described above, with the phantom 1 of the present embodiment, the relative refractive index or the sound speed difference of the background region against the background water can be varied by adjusting the temperature, enabling the phantom to mimic a dense breast or a fatty breast. The sound speed of the inclusion region can be varied by using different solutions. The oil gel representing the background region of the phantom 1 is known to undergo only small deterioration over time (NPL 3), and enables a performance evaluation to be performed on a regular basis over a long time period using the same phantom.

Method of Production of Background Region and Inclusion Region

Figure 12:
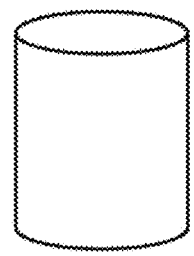
FIGS. 12(a)-12(c) show diagrams representing the shapes of containers used to make the background region.
Figure 12:
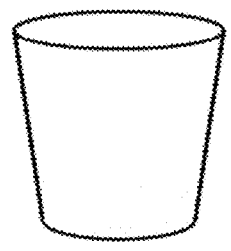
Figure 12:
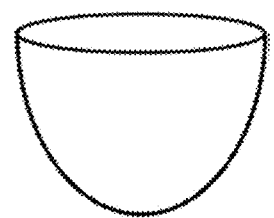

A method for producing the background region and the inclusion region is described below. FIG. 12 shows diagrams representing the shapes of containers used to make the background region. In the embodiment described above, the background region and the inclusion region in the phantom 1 have a columnar shape. The shape of the background region is formed by pouring a solution of SEBS in paraffin oil into a columnar container. A cylindrical background region (oil gel) can be formed with the container shown in FIG. 12(a).

The phantom 1 may have a different shape. A background region (oil gel) of a tapered shape with a top surface larger in diameter than the bottom surface can be produced by pouring a solution of SEBS in paraffin oil into a tapered cup-like container as shown in FIG. 12(b). A background region (oil gel) of a bowl shape can be produced by pouring a solution of SEBS in paraffin oil into a bowl-like container as shown in FIG. 12(c). In this manner, a phantom 1 of a shape having any combination of flat surfaces and/or curved surfaces may be produced by changing the shape of the container that accepts the paraffin oil solution.

Suited as the container material is polypropylene, which can be cut. The inclusion region can be produced by inserting a round-rod mold into the paraffin oil solution before it gels, and cooling the solution. A cylindrical inclusion region is produced upon removing the round rod from the gel. To remove the mold, a narrow spatula is inserted at the area of contact between the mold and the gel with the oil gel being immersed in 30 to 40 degree Celsius water, and the round rod is pulled out while detaching the gel from the mold with the spatula. Examples of materials suited as the round rod include polypropylene, and fluororesin. The diameter of the columnar inclusion region is preferably about 1 to 50 mm, a diameter for mimicking breast cancer.

Figure 13:
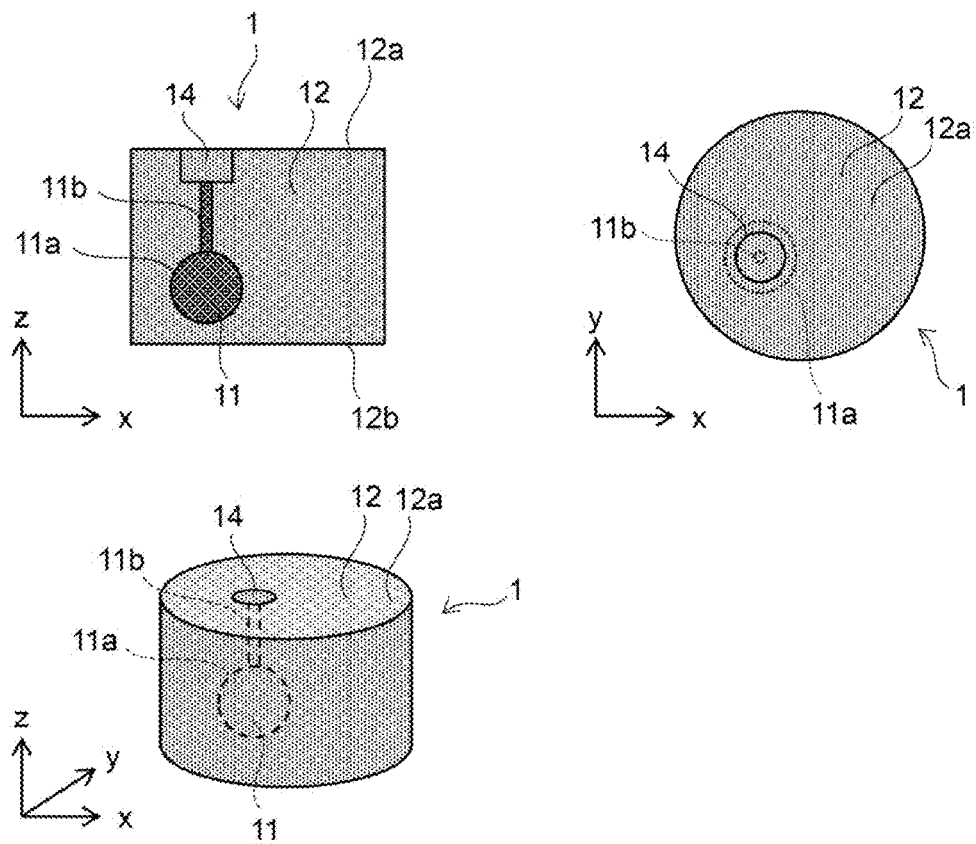
FIG. 13 shows a phantom having a spherical inclusion region according to an embodiment.

FIG. 13 shows a phantom having a spherical inclusion region according to an embodiment. The inclusion region formed in the phantom 1 may be spherical in shape. A spherical inclusion region has a spherical space 11a, and a narrow cylindrical hole 11b connecting the first surface 12a of the second member 12 to the spherical space 11a. The solution is introduced through the hole 11b, and fills the spherical space 11a, producing a spherical first member 11.

The spherical space 11a and the cylindrical hole 11b are produced using a spherical mold having a thin round rod attached to the sphere. The diameter of the spherical space 11a is preferably about 1 to 50 mm. The round rod used to make the hole 11b has a diameter that is preferably no larger than a half of the sphere diameter. As with the case of the cylindrical inclusion region, the spherical space 11a and the hole 11b are produced by inserting the mold in a solution that has not gelled, and removing the mold after the solution has gelled. For removal, the spherical mold is pulled out by stretching the hole 11b with a spatula. Examples of materials suited for the mold include polypropylene, and fluororesin. Because the removal of the mold becomes more difficult as the hole becomes narrower, the mold material may use a water-soluble support material used for 3D printers, or a support material that can be dissolved with limonene. The spherical space and the hole can be produced by inserting the mold in the solution, and dissolving the mold after the solution has gelled. The inclusion region is sealed by disposing a plug 14 in the area (first surface 12a) connecting the hole 11b to outside.

Figure 14:
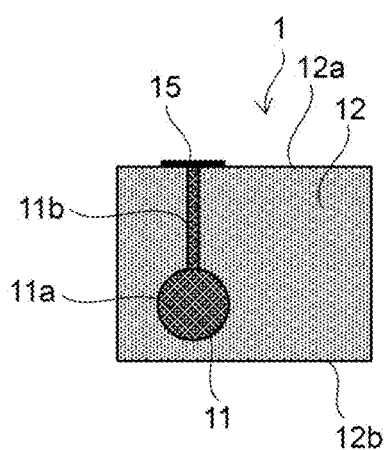
FIG. 14 is a diagram showing a phantom sealed with a film according to an embodiment.

FIG. 14 is a diagram showing a phantom 1 sealed with a film according to an embodiment. The inclusion region may be sealed by disposing a film 15 in the area (first surface 12a) connecting the hole 11b to outside.

Figure 15:
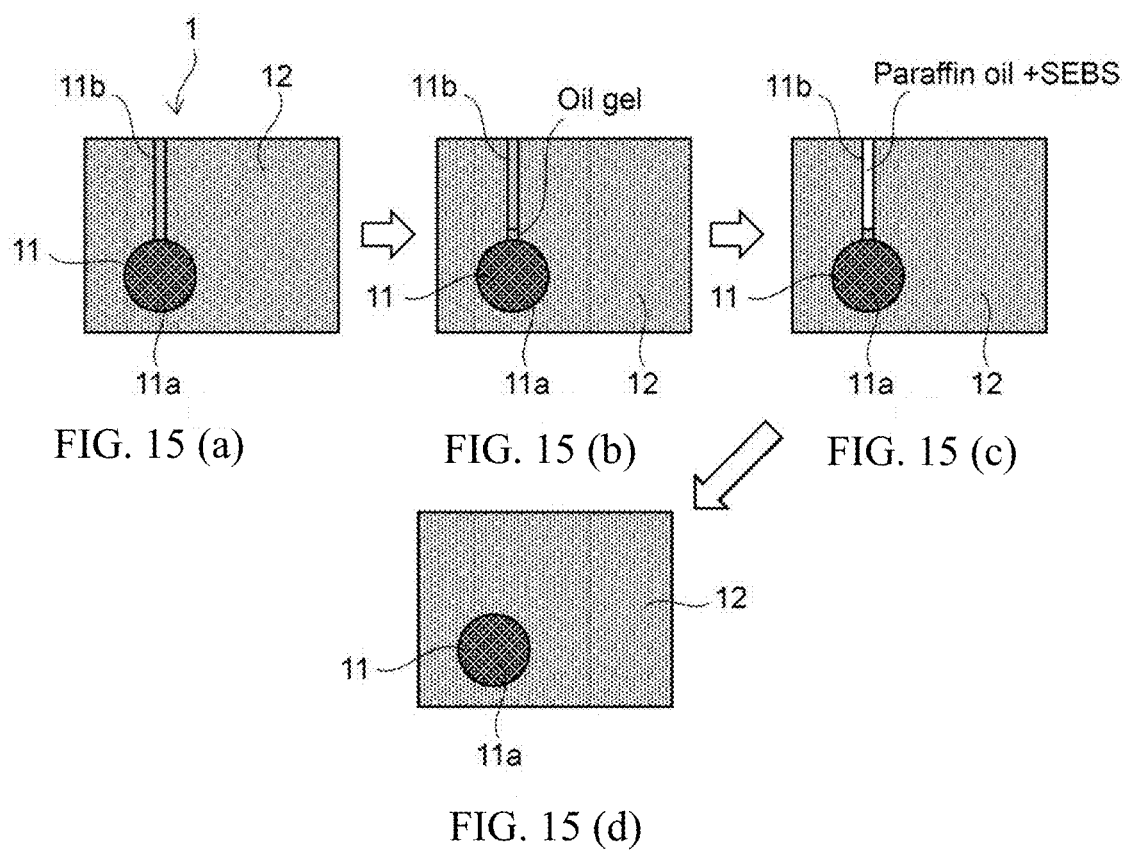
FIGS. 15(a)-15(d) show diagrams representing a method for producing a phantom that does not require an exchange of a solution according to an embodiment.

To exchange the solution, the inclusion region requires a hole for injecting the solution and removing the solution to outside. However, a phantom 1 may be produced that does not involve an exchange of solution. FIG. 15 shows diagrams representing a method for producing a phantom 1 that does not involve an exchange of solution according to an embodiment.

FIG. 15(a) shows the spherical space 11a filled with a solution after the inclusion region is produced in the oil gel. As shown in FIG. 15(b), a cylindrical oil gel having about the same diameter as the hole 11b is disposed directly on the solution. As shown in FIG. 15(c), a solution of SEBS in paraffin oil is injected in the hole 11b. The solution (first member 11) can then be sealed with the paraffin oil solution as it gels, as shown in FIG. 15(d).

Figure 16:
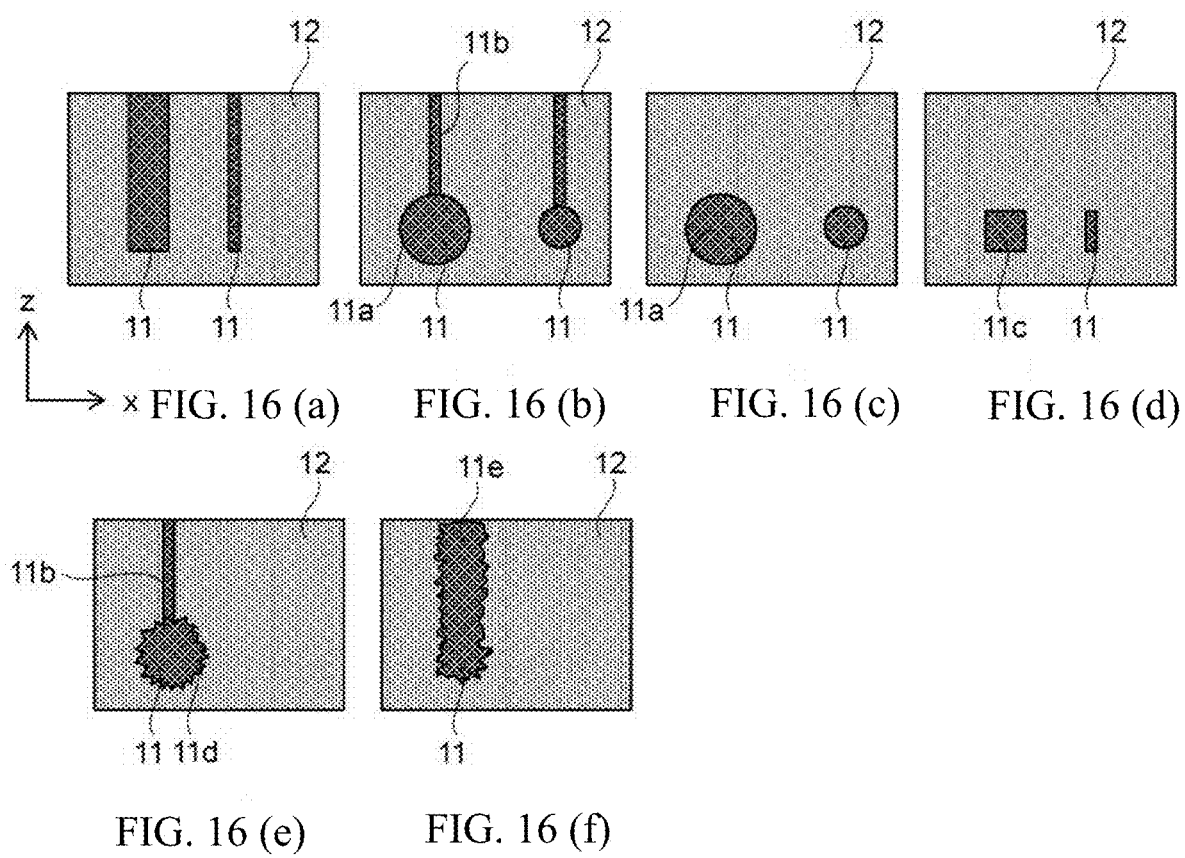
FIGS. 16(a)-16(f) show different forms of inclusion region.

FIG. 16 shows different forms of inclusion region. FIG. 16(a) shows columnar inclusion regions. FIG. 16(b) shows inclusion regions having the spherical space 11a and the hole 11b. FIG. 16(c) shows inclusion regions having only the spherical space 11a inside the oil gel with no injection pathway for the solution. FIG. 16(d) shows inclusion regions having a columnar space 11c inside the oil gel with no injection pathway for the solution. FIG. 16(e) shows an inclusion region having the hole 11b, and a sphere 11d having surface irregularities. FIG. 16(f) shows an inclusion region of a columnar shape 11e having surface irregularities. The inclusion regions shown in FIGS. 16(e) and 16(f) have surface irregularities, and can mimic a tumor having non-smooth boundaries. The inclusion region having surface irregularities can be produced by attaching, for example, a sandpaper, to the mold used to make the inclusion region.

Phantom Material

Figure 17:
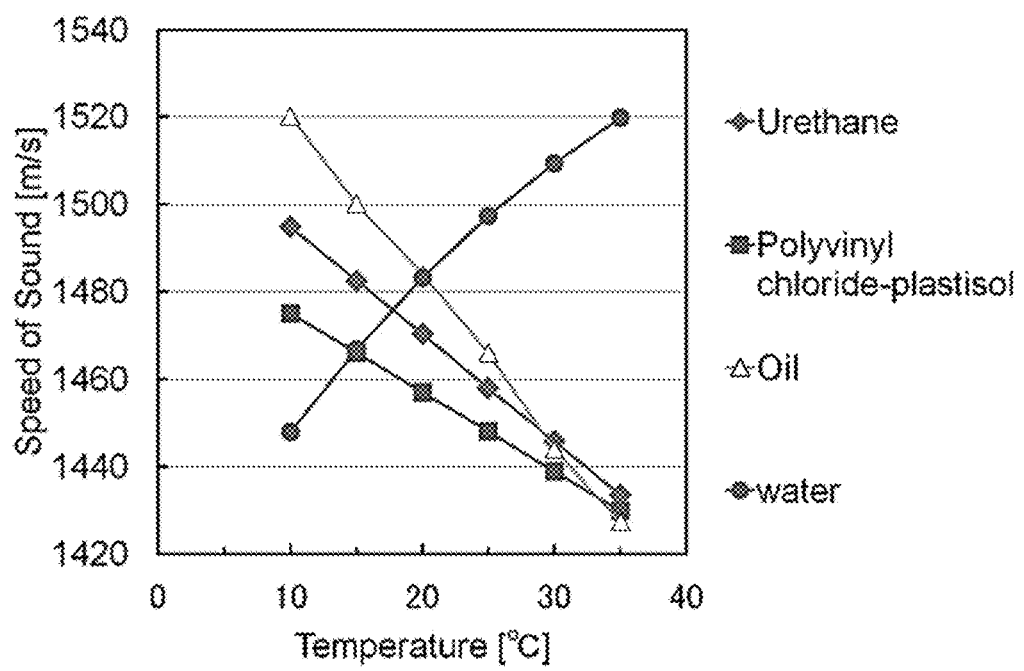
FIG. 17 shows a diagram representing the temperature dependence of the sound speed of various materials.

In the present embodiment, an oil gel is used for the material of the second member 12 (background region) of the phantom 1. Examples of materials other than oil gel include urethane, polyvinyl chloride plastisol (NPL 4, NPL 5). FIG. 17 shows a diagram representing the temperature dependence of the sound speed of various materials. As shown in FIG. 17, the urethane, the oil gel, and the polyvinyl chloride plastisol have the property to decrease their sound speeds with increase in temperature, and have the same sound speed as water at a predetermined temperature. This makes the urethane and the polyvinyl chloride plastisol also usable as material of the second member 12 (background region) of the phantom 1.

Performance Evaluation of Device Using Phantom

Figure 18:
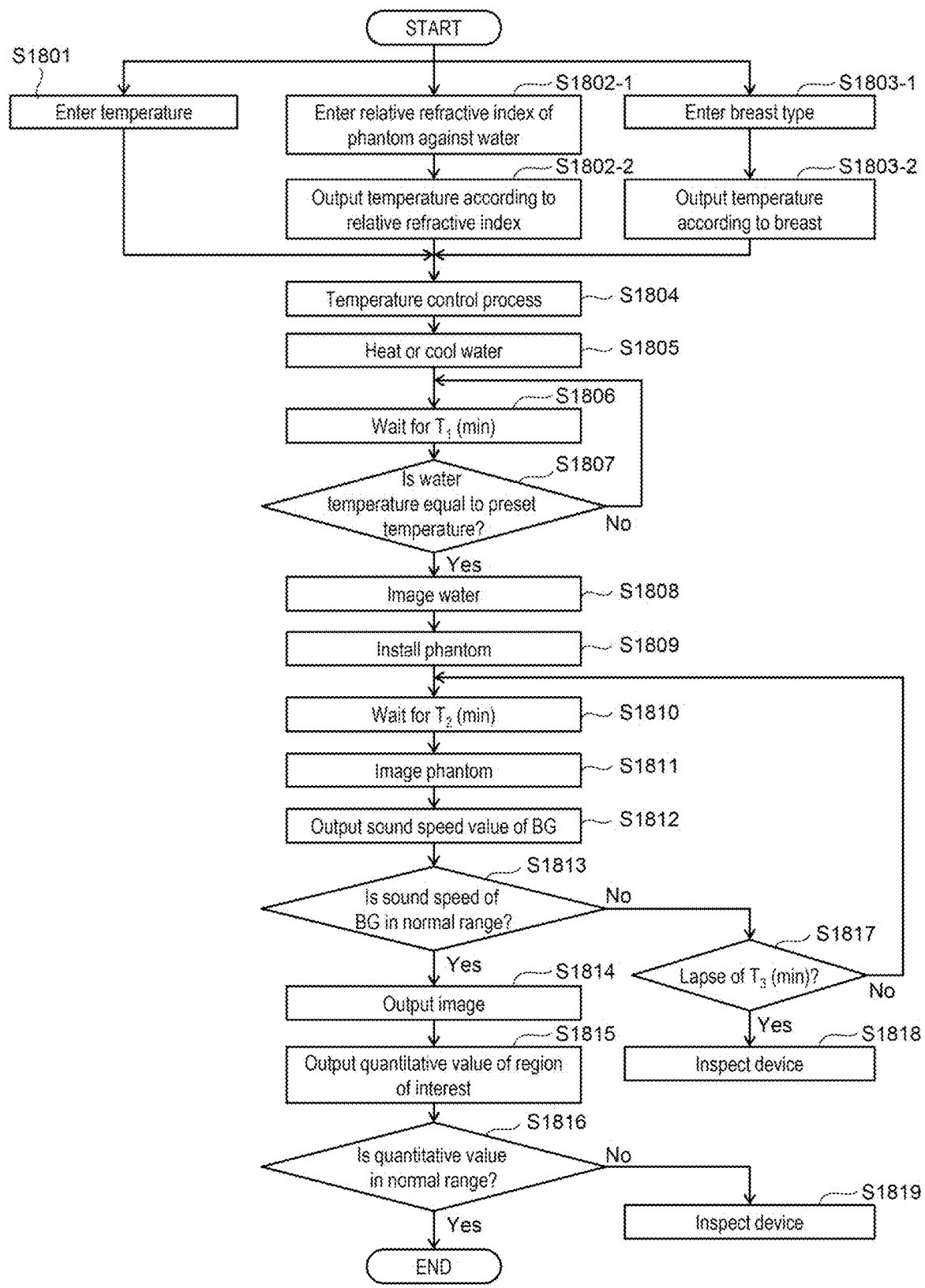
FIG. 18 is a diagram showing a flowchart of a performance evaluation of an ultrasound CT device according to an embodiment.

FIG. 18 is a diagram showing a flowchart of a performance evaluation of the ultrasound CT device 100 according to an embodiment. Here, the phantom 1 using an oil gel described in the foregoing embodiment is used.

First, a user sets a temperature for the measurement of the phantom 1. In this embodiment, the temperature is set in three patterns.

(1) A temperature is directly entered through an interface on a display (S1801)

(2) The relative refractive index or the sound speed difference of the phantom 1 against water is entered through an interface on a display (S1802-1)

(3) A type of breast to be mimicked is selected (S1803-1)

The memory section 8 contains a first table storing the relationship between temperature and the relative refractive index or the sound speed difference of the phantom 1 against water. In the case of (2), the controller 6 outputs a temperature that corresponds to the entered relative refractive index or sound speed difference, using the first table (S1802-2).

The memory section 8 contains a second table storing the relationship between the breast type (for example, four types of extremely dense, heterogeneously dense, scattered fibroglandular, and fatty) and the corresponding relative refractive index or sound speed difference of the phantom 1 corresponding to each type against water. In the case of (3), the controller 6 obtains a relative refractive index or a sound speed difference corresponding to the selected breast type, using the second table, and outputs a temperature that corresponds to the acquired relative refractive index or sound speed difference, using the first table (S1803-2). As another example, the memory section 8 may contain a table storing the relationship between breast types and temperatures corresponding to each type.

After the input made according to any of (1), (2), and (3), the controller 6 executes the temperature control process (S1804). Specifically, the controller 6 controls a temperature adjuster (not illustrated), and heats or cools the water inside the auxiliary tank 5 (S1805). The controller 6 sends the heated or cooled water to the water tank 4.

The controller 6 puts itself in standby for a time period $T_1$ (min) after sending water to the water tank 4 (S1806). After an elapsed time of $T_1$ (min), the controller 6 determines whether the temperature of the water in the water tank 4 is at the preset temperature (S1807). The controller 6 repeats the steps S1806 and S1807 until the temperature reaches the preset temperature.

Upon the temperature of the water in the water tank 4 reaching the preset temperature, the controller 6 controls the signal processor 7 to create an image of data for water to be used as correction data (S1808). The signal processor 7 outputs the image of water from data collected by the ultrasound transmitter and receiver unit array module 3.

After the imaging of water is finished, the phantom 1 is installed in the water tank 4 (S1809). After an elapsed time $T_2$ (min) (S1810), the controller 6 controls the signal processor 7 to create an image of the phantom 1 (S1811). The signal processor 7 outputs the sound speed value in the background region of the phantom 1 (S1812).

The signal processor 7 determines whether the sound speed value in the background region is in the normal range (S1813). Here, the signal processor 7 determines that the sound speed value is in the normal range when the measured sound speed value is in a range of from V−dV to V+dV, where V is the sound speed value in the background region of the phantom 1 at the preset temperature, and dV is the acceptable range.

If the sound speed value is in the normal range in S1813, the signal processor 7 outputs the image of the phantom 1 (S1814). The signal processor 7 then outputs a quantitative value for the region of interest (inclusion region) (S1815). The controller 6 determines whether the quantitative value is in the normal range (S1816). When the quantitative value is in the normal range, the device is determined as being capable of producing an image as normal, and the process is finished. The device is inspected when the quantitative value is outside of the normal range in S1816 (S1819).

When the sound speed value is outside of the normal range in S1813, the controller 6 determines whether a time period $T_3$ (min) has elapsed since the start of phantom imaging (S1817). The steps from S1810 to S1813 are repeated when time $T_3$ (min) has not elapsed. In the event where the sound speed value does not fall in the normal range even after a lapse of $T_3$ (min) since imaging of the phantom started, it means that the phantom 1 has not reached the preset temperature even after a certain length of time. In this case, the device is inspected (S1818).

Figure 19:
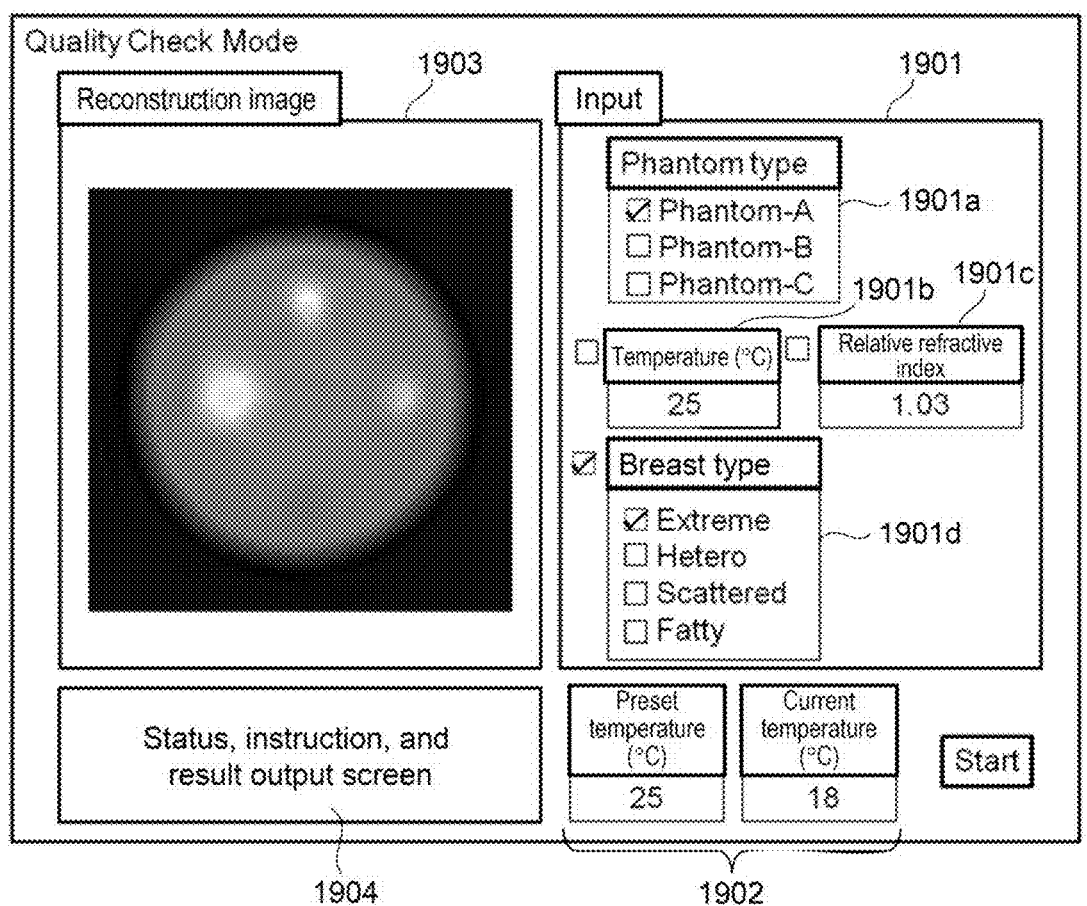
FIG. 19 is a diagram showing a GUI screen used for performance evaluation according to an embodiment.

FIG. 19 is a diagram showing a GUI (graphical user interface) screen used for performance evaluation according to an embodiment. The GUI includes an input region 1901, a temperature display region 1902, a reconstruction image display region 1903, and a result display region 1904 for displaying information such as status and results. The input region 1901 is a region where a user makes an input, and includes a first input section 1901a for inputting the type of the phantom used, a second input section 1901b for inputting a preset temperature, a third input section 1901c for inputting the relative refractive index (or sound speed difference) of the phantom against water, and a fourth input section 1901d for inputting the type of breast.

The type of phantom entered through the first input section 1901a may be based on, for example, (1) the size and shape of the inclusion region, (2) the type of solution, and (3) the size, shape, and material of the background region. The first input section 1901a is configured so that these settings can be selected.

Pushing the "Start" button on the GUI starts the procedures of FIG. 18. The temperature display region 1902 displays the preset temperature using any of the information from the second input section 1901b, the third input section 1901c, and the fourth input section 1901d. The temperature display region 1902 also displays the current temperature of the water tank 4 as soon as water is sent into the water tank 4. The reconstruction image display region 1903 displays a reconstruction image of the phantom 1. The result display region 1904 outputs the current status, instructions, and results, depending on the progression of the procedures shown in FIG. 18.

Standardization Using Phantom

Different facilities use different protocols for clinical imaging of breasts using the ultrasound CT device 100. In order to ensure the accuracy of diagnosis by clinical imaging, standardization is needed for parameters such as imaging conditions, and image processing methods. Ideally, a certain level of diagnosis accuracy should be ensured regardless of the facility conducting imaging.

For standardization, the performance of a device needs to be quantitatively evaluated for different facilities, using the same phantom. The phantom 1 of the embodiment undergoes only small acoustic property changes over a long time period, and can be used for performance evaluations performed for standardization.

As an example, the following conditions are used as the standardization protocol.

The inclusion region in the oil gel/phantom is filled with salty water (3.5%).
Water temperature is set to 25° C.
The mode of ultrasound transmission is a fan beam.
Ultrasound is projected in 256 directions.
FBP (filtered back projection) is used for image reconstruction.
The pixel size of image is 1 mm or less.
Image filter is not used.

The phantom 1 is imaged at different facilities using the ultrasound CT device 100. The ultrasound CT devices 100 at different facilities are connected to one another via a network. For example, image data may be collected by the ultrasound CT devices 100 at different facilities, and at least one statistical information selected from a mean value, a standard deviation, a maximum value, a minimum value, and a median value across the facilities may be calculated with regard to the sound speeds and the attenuations of the background region and the inclusion region. At each facility, the ultrasound CT device 100 displays the content of the standardization protocol, and the statistical information across the facilities. This makes it possible to compare the performance of the device at a given facility with the performance at other facilities. A user is thus able to confirm whether the performance of the ultrasound CT device 100 at his or her facility is at the same level of performance as compared to other facilities. A user may compare the numerical values (the sound speeds and the attenuations of the background region and the inclusion region) of the ultrasound CT device 100 at his or her facility with the statistical information, and inspect the device when the numerical values at his or her facility greatly differ from the statistical information. This contributes to the maintenance of the device, in addition to ensuring diagnosis accuracy.

The standardization protocol is subject to change as the performance of the ultrasound CT device 100 improves, and the statistical information of quantitative values between facilities is updated every time a change is made to the standardization protocol.

Correction of Quantitative Value for Object of Interest for Measurement

The accuracy of the quantitative values of the sound speed and the attenuation imaged by the ultrasound CT device depends on the device's space resolution, which is determined by factors such as the frequency of the transmitted ultrasound, the size of the transmitter and receiver units, and the image reconstruction method. The accuracy of quantitative values decreases as the object of interest for measurement, specifically the tumor region or the inclusion region becomes smaller. The phantom 1 of the present embodiment has the inclusion region filled with a solution, and the sound speed of the inclusion region can be found with accuracy using a premeasured sound speed of the solution. The quantitative values of a tumor obtained by clinical imaging can be corrected in the manner described below.

First, the ultrasound CT device 100 images the phantom 1 having an inclusion region of a spherical shape. The sound speed values of water, the background region, and the inclusion region in the imaged phantom are $S_w(t_p)$, $S_{BG}(t_p)$, and $S_{inc}(t_p, d_{inc}, c)$, respectively. Here, $t_p$ is the temperature of the phantom 1 being measured, $d_{inc}$ is the diameter of the inclusion region, and c is the salty water concentration. The quantitative value has a correction coefficient $f(t_p, d_{inc}, c) = S_{inc}(t_p, d_{inc}, c)/S_{BG}(t_p)$. A ROI (region of interest) is set for the reconstruction image of the phantom, with water, the background region, and the inclusion region having ROI values of $ROI_w(t_p)$, $ROI_{BG}(t_p)$, and $ROI_{inc}(t_p, d_{inc}, c)$, respectively. Because water and the background region can take a wide range of ROI, it can be assumed that $ROI_w(t_p) = S_w(t_p)$, and $ROI_{BG}(t_p) = S_{BG}(t_p)$. The proportion of the background region relative to water is $r_1^P(t_p) = ROI_{BG}(t_p)/ROI_w(t_p)$, and the proportion of the inclusion region relative to the background region is $r_2^P(t_p, d_{inc}, c) = ROI_{inc}(t_p, d_{inc}, c)/ROI_{BG}(t_p)$.

For imaging, for example, a phantom having inclusion regions measuring 3, 5, 7, 10, 15, and 20 mm in diameter is measured at varying temperatures of 15, 17.5, 20, 22.5, 25, and 27.5° C., and at varying salty water concentrations of 0, 1, 2, 3, 4, 5, 6, 7, 8% in the imaged phantom. The ultrasound CT device 100 determines $f(t_p, d_{inc}, c)$, $r_1^P(t_p)$, and $r_2^P(t_p, d_{inc}, c)$ for all temperatures, diameters, and salty water concentrations. In this manner, the ultrasound CT device 100 calculates correction data as it creates an image at different temperatures and different solution concentrations for the inclusion regions of different sizes. The correction data so determined are stored in the memory section 8.

For clinical imaging, sound speed values $S_w(t_h)$, $S_{bre}$, and $S_{can}(d_{can})$ are set for water, a breast, and a tumor region. Here, $t_h$ is the temperature at the time of clinical imaging, and $d_{can}$ is the diameter of when the tumor is approximated to a sphere. A ROI is set for the reconstruction image produced by clinical imaging, with water, the breast, and the tumor having ROI values of $ROI_w(t_h)$, $ROI_{bre}$, and $ROI_{can}(d_{can})$, respectively. Because water and breast can take a wide range of ROI, it can be assumed that $ROI_w(t_h) = S_w(t_h)$, and $ROI_{bre} = S_{bre}$. The proportion of the breast region relative to water is $r_1^h(t_h) = ROI_{bre}/ROI_w(t_h)$, and the proportion of the tumor region relative to the breast region is $r_2^h(d_{can}) = ROI_{can}(d_{can})/ROI_{bre}$. The temperature at which $r_1^P(t_p)$ is closest to $r_1^h(t^h)$ is $t_p'$. The $d_{inc}$ value that is closest to the tumor diameter $d_{can}$ is $d_{inc}'$. The salty water concentration at which $r_2^P(t_p', d_{inc}', c)$ is closest to $r_2^h(d_{can})$ is $c'$. The ultrasound CT device 100 determines the corrected quantitative value for the tumor region by $ROI_{bre} \times f(t_p', d_{inc}', c')$. With this configuration, the ultrasound CT device 100 can correct the quantitative value of the clinically imaged tumor using the previously determined correction data.

The phantom 1 for ultrasound measurement of the present embodiment includes the first member (inclusion region) 11 that mimics an object of interest for measurement, and the second member (background region) 12 having provided therein the first member 11. The properties of the first member 11 and the second member 12 are such that these are not miscible with each other. The second member 12 has the property to decrease its sound speed with a temperature increase brought by external temperature control, and the sound speed of the second member 12 at the predetermined temperature $T_0$ is the same as the sound speed of the third member 13 (the solution in the water tank 4) surrounding the second member 12. With such a configuration, the second member 12 of the phantom 1 has a higher sound speed than the third member 13 at a temperature below $T_0$, enabling the phantom 1 to mimic a dense breast. At a temperature higher than $T_0$, the second member 12 has a lower sound speed than the third member 13, enabling the phantom 1 to mimic a fatty breast.

The present invention is not limited to the embodiments described above, and includes many variations. The foregoing embodiments were described to help illustrate the present invention, and the invention is not necessarily required to include all of the configurations described above. A part of the configuration of a certain embodiment may be replaced with the configuration of some other embodiment. It is also possible to add the configuration of a certain embodiment to the configuration of some other embodiment. It is also possible to add other configuration to a part of the configurations of the embodiments, or delete and/or replace a part of the configurations of the embodiments.

The functions of the controller 6 and the signal processor 7 may be implemented by software, specifically a processor interpreting and executing programs provided to implement the functions of these members. Information including programs and files for implementing functions may reside in memory, storage devices such as hard disc and SSD (Solid State Drive), or storage media such as IC cards, SD cards, and DVD. The foregoing functions may be implemented, either in part or as a whole, by hardware, for example, hardware designed with integrated circuits.

The control lines and information lines used in the embodiments above merely represent lines that are considered to be necessary for the purpose of explanation, and do not necessarily represent the all control lines and information lines of a product. All configurations may be interconnected to one another.

REFERENCE SIGNS LIST

1: Phantom for ultrasound measurement
2: Bed
3: Ultrasound transmitter and receiver unit array module
4: Water tank
5: Auxiliary tank
6: Controller
7: Signal processor
8: Memory section
9: Input-output section
11: First member of phantom
12: Second member of phantom
13: Third member surrounding phantom
14: Plug
15: Film
100: Ultrasound CT device

The invention claimed is:

1. An ultrasound CT device, comprising:
a phantom for ultrasound measurement, comprising:
   a first member that mimics an object of interest for measurement; and
   a second member having provided therein the first member,
   the second member configured to decrease its sound speed with a temperature increase brought by external temperature control, the sound speed of the second member at a predetermined temperature being equal to a sound speed of a third member surrounding the second member,
   the first member and the second member being immiscible with each other;
an input-output section capable of setting a preset temperature, a relative refractive index of the second member for a wave against the third member, or a breast type; and
a controller configured to control a temperature of the third member surrounding the second member, according to at least one of the preset temperature, the relative refractive index of the second member for a wave against the third member, and the breast type, and
wherein the controller calculates correction data by creating an image at varying temperatures and at varying solution concentrations for more than one size of the first member, and the controller uses the correction data to correct a quantitative value of a tumor obtained by clinical imaging.

2. The ultrasound CT device of claim 1, wherein the second member is one of an oil gel, urethane, and polyvinyl chloride plastisol.

3. The ultrasound CT device of claim 1, wherein the first member is liquid.

4. The ultrasound CT device of claim 3, wherein the liquid is one of water and salty water.

5. The ultrasound CT device of claim 4, wherein the salty water has a concentration that is higher than 0% and not more than 8%.

6. The ultrasound CT device of claim 1, wherein the third member is water.

7. The ultrasound CT device of claim 1, wherein the first member has a columnar shape or a spherical shape.

8. The ultrasound CT device of claim 1, wherein the first member has a surface with irregularities.

9. The ultrasound CT device of claim 3, wherein the phantom further comprises a plug or a film configured to seal the liquid.

10. The ultrasound CT device of claim 3, wherein the first member is embedded in the second member without being exposed at a surface of the second member.

11. The ultrasound CT device of claim 1, wherein the second member has one of a columnar shape, a tapered cup shape, and a bowl shape.

12. The ultrasound CT device of claim 1,
wherein the controller controls the temperature of the third member, and sets a value of 0.9 to 1.05 for the relative refractive index of the second member for a wave against the third member.

13. The ultrasound CT device of claim 1,
wherein the controller calculates at least one statistical information selected from a mean value, a standard deviation, a maximum value, a minimum value, and a median value across a plurality of facilities with regard to sound speeds and attenuations of the first member and the second member, and
wherein the input-output section displays said at least one statistical information on a screen of the ultrasound CT device.

* * * * *